United States Patent
Onodera et al.

(10) Patent No.: US 7,335,784 B2
(45) Date of Patent: Feb. 26, 2008

(54) METHOD FOR DISTILLATION OF ORGANOSILICON COMPOUNDS THAT CONTAIN ACRYLOXY OR METHACRYLOXY GROUPS

(75) Inventors: Satoshi Onodera, Chiba Prefecture (JP); Tadashi Okawa, Chiba Prefecture (JP)

(73) Assignee: Dow Corning Toray Company, Ltd., Chiyoda-Ku Tokyo (JP)

( * ) Notice: Subject to any disclaimer, the term of this patent is extended or adjusted under 35 U.S.C. 154(b) by 0 days.

(21) Appl. No.: 10/550,822

(22) PCT Filed: Mar. 19, 2004

(86) PCT No.: PCT/JP2004/003786

§ 371 (c)(1),
(2), (4) Date: Jul. 17, 2006

(87) PCT Pub. No.: WO2004/085446

PCT Pub. Date: Oct. 7, 2004

(65) Prior Publication Data

US 2007/0004930 A1    Jan. 4, 2007

(30) Foreign Application Priority Data

Mar. 25, 2003   (JP)   ............... 2003-081936

(51) Int. Cl.
*C07F 7/08*   (2006.01)
(52) U.S. Cl. .................................... 556/440
(58) Field of Classification Search ............ None
See application file for complete search history.

(56) References Cited

U.S. PATENT DOCUMENTS

| | | | |
|---|---|---|---|
| 3,801,615 A | 4/1974 | Chuang | |
| 5,262,555 A | 11/1993 | Okawa et al. | |
| 5,723,643 A | 3/1998 | Mikami et al. | |
| 5,914,418 A | 6/1999 | Mikami et al. | |

FOREIGN PATENT DOCUMENTS

| | | |
|---|---|---|
| DE | 102 49 637 | 12/2003 |
| EP | 0 562 584 | 9/1993 |
| EP | 0 520 477 | 3/1997 |
| EP | 0 803 507 | 10/1997 |
| JP | 48-85501 | 11/1973 |
| JP | 5-186478 | 7/1993 |
| JP | 5-271248 | 10/1993 |
| JP | 9-295987 | 11/1997 |
| JP | 9-296007 | 11/1997 |

OTHER PUBLICATIONS

English language Abstract for DE 102 49 637 extracted from espacenet.com database dated Jul. 5, 2006.
English language Abstract for JP5-186478 extracted from espacenet.com database dated Jul. 5, 2006.
English language Abstract for JP 5-271248 extracted from espacenet.com database dated Jul. 5, 2006.
English language Abstract for JP 9-295987 extracted from espacenet.com database dated Jul. 5, 2006.
English language Abstract for JP 9-296007 extracted from espacenet.com database dated Jul. 5, 2006.
English language Abstract for JP 48-85501 extracted from espacenet.com database dated Jul. 5, 2006.

*Primary Examiner*—Samuel A Barts
(74) *Attorney, Agent, or Firm*—Howard & Howard Attorneys, P.C.

(57) ABSTRACT

A method for distillation of organosilicon compounds that contain acryloxy or methacryloxy groups characterized by subjecting an organosilicon compound (A) that contains acryloxy or methacryloxy groups to distillation in the presence of a polymerization inhibitor (B) and a compound (C) with aliphatic conjugated unsaturated bonds.

11 Claims, No Drawings

METHOD FOR DISTILLATION OF ORGANOSILICON COMPOUNDS THAT CONTAIN ACRYLOXY OR METHACRYLOXY GROUPS

RELATED APPLICATIONS

This application claims priority to and all the advantages of International Application No. PCT/JP2004/003786, filed on Mar. 19, 2004, which claims priority to Japanese Patent Application No. 2003-081936, filed on Mar. 25, 2003.

TECHNICAL FIELD

The present invention relates to a method for distillation of organosilicon compounds that contain acryloxy or methacryloxy groups, and more specifically to a method for distillation of the aforementioned compounds, wherein, in spite of the fact that distillation is carried out in the presence of such inhibitors as hindered phenols or hindered-phenol precursors that have an onium-salt structure, the process proceeds without coloration, and the distillation fraction is obtained as a colorless organosilicon compound that contains acryloxy or methacryloxy groups.

BACKGROUND ART

It is known that organosilicon compounds that contain acryloxy or methacryloxy groups react with radical-polymerizable monomers such as methylmethacrylate and styrene and are used as starting materials for copolymers obtained from the aforementioned monomers or as modifiers for the aforementioned monomers.

A method known in the art for synthesis of the aforementioned organosilicon compounds that contain acryloxy or methacryloxy groups consists of causing an addition reaction between acryloxy or methacryloy acid esters of phenols or alcohols with aliphatic unsaturated bonds and organosilicon compounds that contain silicon-bonded hydrogen atoms, and then separating the organosilicon compounds with acryloxy or methacryloxy groups from the obtained reaction mixture by distillation. The organosilicon compounds with acryloxy or methacryloxy groups obtained by the above-described method are prone to polymerization and to an increase in the molecular weight that can easily occur during reaction of synthesis or in the step of distillation. For suppressing the undesired polymerization, radical polymerization inhibitors are generally added.

For example, Japanese Laid-Open Patent Application Publication (hereinafter referred to as "Kokai") Hei 5-186478 (equivalent to EP0520477) discloses a method with the use of N,N-dialkylaminomethylenephenols as polymerization inhibitors. Furthermore, Kokai Hei 9-295987 and Kokai Hei 9-296007 (equivalent to EP0803507), disclose processes with the use of polymerization inhibitors in the form of hindered phenols having an onium-salt structure. These inhibitors are naturally colorless and possess extremely high polymerization-inhibiting power. However, when organosilicon compounds that contain acryloxy or methacryloxy groups undergo distillation in the presence of the aforementioned polymerization inhibitors, the distillation fractions are subject to coloration, and it becomes very difficult to obtain colorless distillation fractions of high purity.

Kokai Sho 48-85501 (equivalent to U.S. Pat. No. 3,801,615) discloses a method for decoloration of benzoquinone, which is a coloring component, by adding an olefinic unsaturated conjugated diene to oxidation-polymerizable monoolefinic unsaturated monomer synthesized by distillation with the use of hydroquinone as an inhibitor. However, the use of hindered phenols in the above method as polymerization inhibitors cannot prevent coloration of the distillation fractions. this occurs, probably, because the benzoquinone and the coloring substance admixed with the distillation fraction have different structures.

It is an object of the present invention to provide a method for inhibiting coloration of products of distillation of organosilicon compounds with acryloxy or methacryloxy groups when the distillation is carried in the presence of polymerization inhibitors in the form of hindered phenols having an onium-salt structure or their hindered phenol precursors.

DISCLOSURE OF INVENTION

The present invention relates to a method for distillation of organosilicon compounds that contain acryloxy or methacryloxy groups characterized by subjecting an organosilicon compound (A) that contains acryloxy or methacryloxy groups to distillation in the presence of a polymerization inhibitor (B) of the following general formula (1):

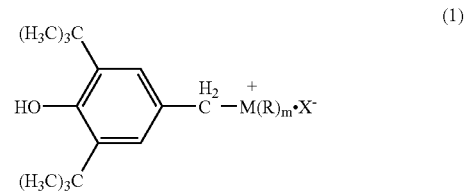

or of the following chemical formula (2):

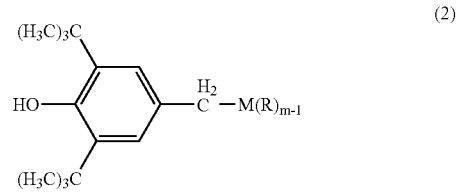

(where, M is an atom selected from the group consisting of N, P, As, Sb, O, S, Se, Sn and I; R is a monovalent hydrocarbon group or a hydrogen atom; m is 1, 2 or 3; and X is a conjugated base of an organic acid or inorganic acid) and a compound (C) with aliphatic conjugated unsaturated bonds.

BEST MODE FOR CARRYING OUT THE INVENTION

The invention will be further described in more detail.

There are no special restrictions with regard to the structure of the organosilicon compound (A) that contains acryloxy or methacryloxy groups, except that it should contain acryloxy or methacryloxy groups and should have a boiling point that provides isolation under the effect of distillation.

The following are examples of the aforementioned organosilicon compound: 3-methacryloxypropyl-dimethylchlorosilane, 3-methacryloxypropyl-methyldichlorosilane, 3-methacryloxypropyl-trichlorosilane or similar chlorosilanes that contain methacryloxy groups; 3-acryloxypropyl-dimethylchlorosilane, 3-acryloxypropylmethyl-dichlorosilane, 3-acryloxypropyl-trichlorosilane, or similar chlorosilanes that contain acryloxy groups; 3-methacryloxypropyl-dimethylmethoxysilane, 3-methacryloxypropyl-methyldimethoxysilane, 3-methacryloxypropyl-trimethoxysilane, 3-methacryloxypropyl-dimethylethoxysilane, 3-methacryloxypropyl-methyldiethoxysilane, 3-methacryloxypropyl-triethoxysilane, or similar alkoxysilanes that contain methacryloxy groups; 3-acryloxypropyl-dimethyl-methoxysilane, 3-acryloxypropylmethyl-dimethoxysilane, 3-acryloxypropyl-trimethoxysilane, 3-acryloxyropyl-dimethylethoxysilane, 3-acryloxypropyl-methyldiethoxysilane, 3-acryloxypropyl-triethoxysilane or similar alkoxysilanes that contain acryloxy groups; 1,3-bis (methacryloxypropyl) tetramethyldisiloxane, (methacryloxypropyl) pentamethyldisiloxane, methacryloxypropyl-tris (trimethylsiloxy) silane or similar siloxane oligomers that contain methacryloxy groups; 1,3-bis (acryloxypropyl) tetramethyldisiloxane, acryloxypropyl-pentamethyldisiloxane, acryloxypropyl tris (trimethylsiloxy) silane or similar siloxane oligomers that contain acryloxy groups.

Component (A) can be synthesized by a known method which is described, e.g., in Kokai 5-186478 and Kokai 9-295987. According to an appropriate method, an acrylic or methacrylic acid ester of phenol or an alcohol with aliphatic unsaturated bonds and alkoxysilane or chlorosilane with silicon-bonded hydrogen atoms are subjected to a hydrosilation reaction in the presence of component (B). Furthermore, for obtaining siloxane oligomers that contain acryloxy or methacryloxy groups, low-molecular-weight alkoxysilanes or chlorosilanes with acryloxy or methacryloxy groups can be either subjected to hydrolysis and condensation, or caused to react with linear-chain, cyclic, or branched organosiloxane oligomers in the presence of an acidic catalyst.

A polymerization inhibitor that constitutes component (B) is intended for inhibiting polymerization and increase in molecular weight during synthesis and/or distillation of aforementioned component (A). Component (B) can be represented by hindered phenols expressed by the following general formulae:

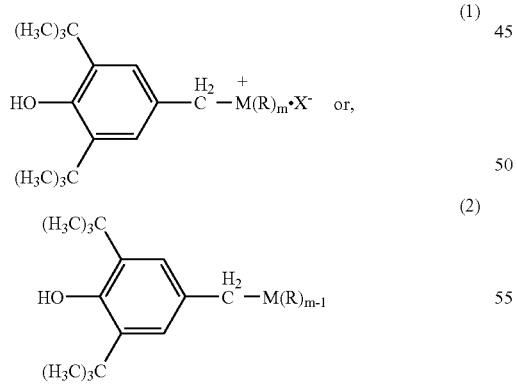

(where, M is an atom selected from the group consisting of N, P, As, Sb, O, S, Se, Sn and I; R is a univalent hydrocarbon group or hydrogen atom; m is 1, 2 or 3; X is a conjugated base of an organic or inorganic acid). In the above formula, R may designate a hydrogen atom or a univalent hydrocarbon group such as methyl group, ethyl group, propyl group, or a similar alkyl group; vinyl group, allyl group, butenyl group, or a similar alkenyl group; phenyl group, tolyl group, xylyl group, or a similar aryl group; phenethyl group, diphenylmethyl group, or a similar aralkyl group. Of these, most preferable are alkyl group or hydrogen atoms, especially alkyl groups and hydrogen atoms. In the above formula, M may designate an atom selected from the group consisting of N, P, As, Sb, O, S, Se, Sn and I; m may be 1, 2 or 3, but when M is N, P, As, or Sb, m is 3, when M is O, S, Se, or Sn, m is 2, and when M is I, m is 1. X designates a conjugated base of an organic or inorganic acid and may comprise a halide ion in the form of a conjugated base of hydrogen chloride, hydrogen bromide, or the like, a conjugated base of acetic acid, propionic acid, acrylic acid, or a similar carboxylic acid, as well as a conjugated base of a sulfonic acid or phosphoric acid.

Appropriate compounds are exemplified by the following chemical structures, where R and X are the same as defined above:

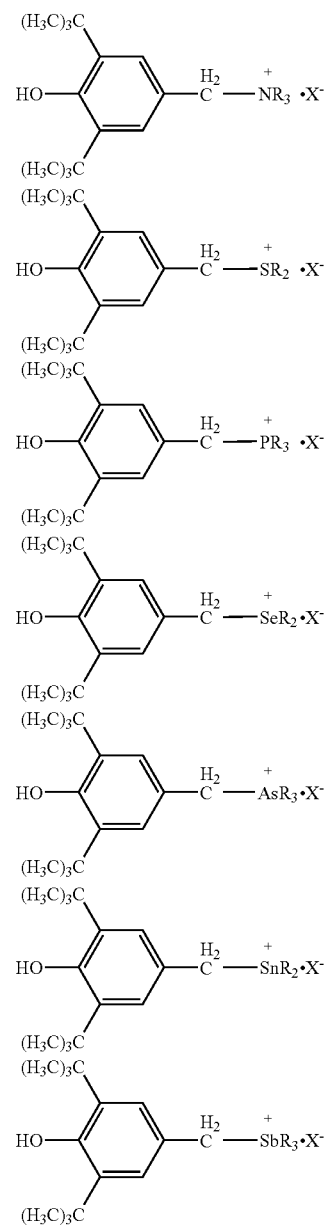

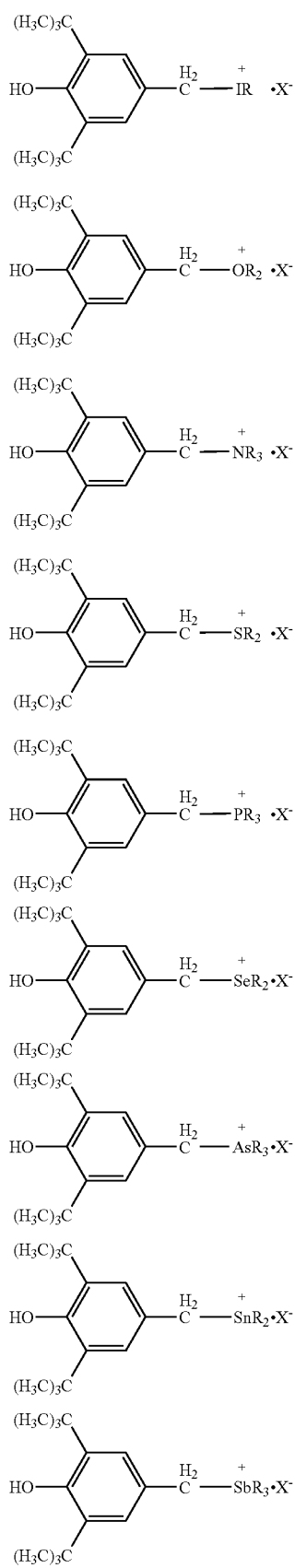

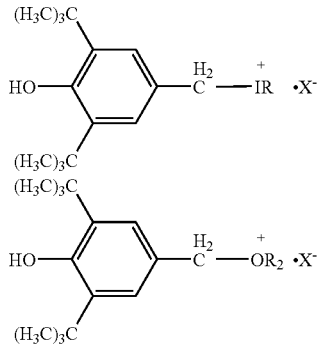

Component (B) may have chemical structures shown above, of which those given below are most preferable (in the following formulae R designates hydrogen atom or the same univalent hydrocarbon group as defined above).

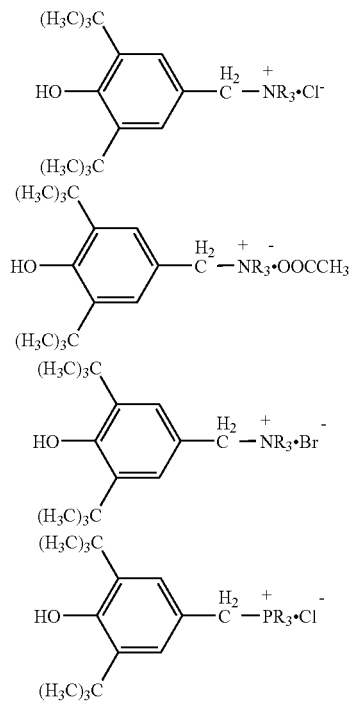

Those of the aforementioned compounds that comprise hindered phenols with an onium salt structure can be easily synthesized by a known method that consists of reacting hindered phenols, having an appropriate Lewis base structure, with an organic or inorganic acid or an organic halide.

The following compounds are most suitable for component (B) from the point of view of availability and ease of synthesis:

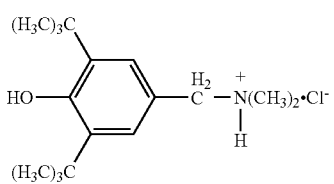

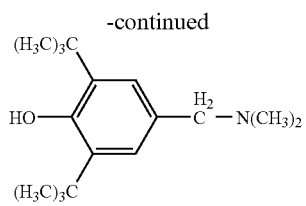

An effective amount of component (B) that should be added to the process depends on conditions of the synthesis reaction and distillation, but, in general, the added amount should be within the range of 0.001 wt. % to 10 wt. %.

A compound with aliphatic conjugated unsaturated bonds that constitutes component (C) is intended for capturing coloring components generated in the aforementioned component (B) with its conjugated unsaturated bonds, and forming into adducts with a high boiling point, and are not admixed with the distillation fractions.

The following are examples of compounds suitable for use as component (C): butadiene, piperylene, isoprene, cyclopentadiene, 2-phenylbutadiene, bicyclohexene, 2,3-dimethylbutadiene, 1,3-cyclohexadiene, 1-phenylbutadiene, 9,10-dimethylanthracene, 1,2-dimethylidenecyclohexane, 1,2-diethylidenecyclohexene, 1-methoxybutadiene, 1,1'-bi-cyclopentene, conjugated linolic acid, dehydrated castor oil, or similar conjugated diene-structure compounds; alloo-cimene, tung oil, α-eleostearic acid or a similar conjugated toriene-structure compound; cyclooctatetraene, or a similar conjugated tetraene-structure compound.

In some distilling condition, if the adduct with a coloring substance and component (C) have low boiling points, it would be impossible to obtain a colorless fraction of distillation due to contamination of them with distillation fraction depending upon distillation conditions, and therefore it is necessary to provide component (C) with as high boiling point as possible. From this point of view, it is recommended to use a conjugated linolic acid, dehydrated castor oil, tung oil, α-eleostearic acid, and cyclooctatetraene. Of these, α-eleostearic acid, and cyclooctatetraene are most preferable as they have conjugated triene structures or conjugated tetraene structures highly reactive with coloring substances, while a tung oil is most preferable from the point of view of availability.

It is recommended to use component (C) in an excess of the amount only needed for obtaining a colorless fraction. The minimal amount required for the process will depend on many factors, such as the quantity and chemical structure required for the target organosilicon compound with acryloxy or methacryloxy groups, the boiling point, the quantity and the boiling point required for the target compound, as well as on the chemicals structure, boiling point, and other characteristics of component (C) itself. In general, however, component (C) should be used in an amount from 0.1 wt. % to 3000 wt. % relative to the weight of component (B).

During distillation, component (C) can be used alone or in combination with inorganic powders, glass beads, carbon black or other substances that can absorb (C) on their surfaces or fix component (C) with a chemical bond on their surfaces. In the last-mentioned case, component (C) can be represented by a lower-melting-point compound. If component (C) is fixed with chemical modification on the surface of such additives, it is required that the residual group contain aliphatic conjugated unsaturated bonds.

It is recommended that distillation of component (A) be conducted under low pressure and at a temperature as low as possible. This is because the above condition facilitates suppression of polymerization and increase in molecular weight, allows for decrease in the amount of the added polymerization inhibitor, and allows for decrease in the amount of coloring substance formed during distillation. For example, distillation can be carried out under pressure below 3000 Pa, preferably below 1500 Pa, and at a temperature between 80 and 150° C., preferably between 100 and 130° C.

In the distillation process, polymerization and increase in the molecular weight of component (A) may be further inhibited by additionally compounding components (B) and (C) with metal halides disclosed in Kokai 5-271248. Such a metal halide may comprise, e.g., copper chloride. Other additives may comprise known antioxidants such as hindered phenol compounds (except for component (B)), amine-type compounds, quinone-type compounds, or the like. Of these, most preferable are hindered phenols (except for component (B)). Although there are no restrictions with regard to the amounts in which the aforementioned antioxidants can be used, it is recommended that their amount in the reaction mixtures with component (A) be within the range of 01-10 wt. %. The use of copper chloride and antioxidants is especially advantageous when component (A) is represented by 3-methacryloxypropyl-dimethylchlorosilane.

In spite of the fact that normally the use of onium-structured hindered phenols and their precursors that possess strong polymerization inhibiting capacity is accompanied by coloration of distillation fractions, the distillation method of the invention makes it possible to obtain organosilicon compounds with acryloxy and methacryloxy groups which are colorless even with the use of the aforementioned high-capacity inhibitors. Since the organosilicon compounds with acryloxy and methacryloxy groups obtained by the method of the invention are colorless, by reacting them with radical-polymerizable monomers, it is possible to prepare starting material for copolymers that can be derived from such monomers or to prepare modifiers for polymers obtained from the aforementioned monomers. In other words, the aforementioned organopolysiloxanes may find application in the fields of industry that requires optically colorless properties.

EXAMPLES

The invention will be further described with reference to application examples. In order to quantitatively evaluate the color of the fractions obtained after distillation, the light absorbance of the fractions was measured with the use of an UV spectro photometer at a wavelength of 350 nm. In observation with the naked eye, the fraction with absorbance below 0.055 at 350 nm wavelength was seen as completely colorless.

Reference Example 1

[Preparation of Hydrochloride of N,N-Dialkylaminomethylenephenol]

A transparent liquid solution was prepared by mixing 1 g (3.8 mmol) of 2,6-di-t-butyl-4-dimethylaminomethylphenol, 0.76 g (8.4 mmol) of trimethylsilanol and 30 ml of toluene. While the mixture was stirred, 0.46 g (4.2 mmol) of trimethylchlorosilane were added to the mixture dropwise, whereby a white precipitate was formed. The product was stirred for 30 min. at room temperature, and the white precipitate was separated by filtering. The obtained white precipitate was washed with toluene and then dried in vacuum for 1 hour at 80° C. The weight of the obtained white precipitate was 0.7 g. Nuclear magnetic resonance (NMR) analysis and infra-red (IR) light-absorption analysis of the white precipitate showed that it was hydrochloride of 2,6-di-t-butyl-4-dimethylaminomethylenephenol having the following chemical structure:

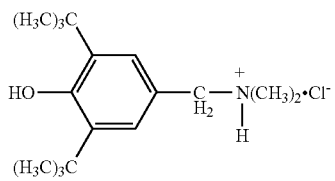

Reference Example 2

[Synthesis of Methacryloxypropyl Dimethylchlorosilane]

A four-neck flask equipped with a stirrer was loaded with 1000 g (7.92 mole) of allyl methacrylate (AMA) (the product of Mitsubishi Gas Chemical Co., Ltd.) and 1.5 g of the hydrochloride of 2,6-di-t-butyl-4-dimethylaminomethyl-enephenol prepared in aforementioned Reference Example 1. The mixture was then combined and further mixed with a complex of platinum and 1,3-divinyltetramethyldisiloxane (the content of metallic platinum was 20 ppm per total weight of the allyl methacrylate and dimethylchlorosilane). While the mixture was stirred and heated at 80° C., a small amount of dimethylchlorosilane was added dropwise. After verification of the fact that reaction has been initiated, the reaction system was cooled by water or by air, and the temperature was maintained within the range of 65-75° C., 682 g (7.2 mole) while dimethylchlorosilane were added dropwise. When the addition process was over, the product was stirred for 1 hour at 70° C. A small sample was taken from the reaction mixture. The area percent of the gas chromatography (GLC) peak of obtained methacryloxypropyl dimethylchlorosilane was 70%.

Application Example 1

A four-neck flask equipped with a stirrer was loaded with 400 g of the reaction mixture obtained in Reference Example 2, 0.2 g of 2,6-di-t-butyl-4-methylphenol, 4 g of Copper(II) chloride, anhydrous and 4 g of tung oil (the product of Kimura Shoji), and the mixture was subjected to distillation in a 10 cm-long Vigreux column under a reduced pressure of 1330 Pa. The residue comprised 50 g of a low-viscosity brown liquid. 190 g of the 110-120° C. distillation fraction was sampled. Gas chromatography analysis of the sample showed that the obtained colorless fraction comprised 3-methacryloxypropyl-dimethylchlorosilane. GLC purity of the product was 97.0%. Absorbance of the obtained 3-methacryloxypropyl-dimethylchlorosilane measured at 350 nm was 0.028.

Application Example 2

Distillation was carried out under the same conditions as in Application Example 1, with the exception that the tung oil was replaced by the same quantity of a linolic acid (the product of KF TRADING Co.,LTD, tradename Hy-Diene). The residue comprised 56 g of a low-viscosity brown liquid. 198 g of the obtained colorless distillation fraction was analyzed by gas chromatography analysis that showed that the product comprised 3-methacryloxypropyl-dimethylchlorosilane. GLC purity of the product was 97.1%. Absorbance of the obtained 3-methacryloxypropyl dimethylchlorosilane measured at 350 nm was 0.042.

Application Example 3

Distillation was carried out under the same conditions as in Application Example 1, with the exception that the tung oil was replaced by the same quantity of a dehydrated castor oil (the product of IU TRADING Co.,LTD, tradename Dassui Himashiyu [Dehydrated Castor Oil]). The residue comprised 64 g of a low-viscous brown liquid. 198 g of the obtained colorless distillation fraction was analyzed by gas chromatography analysis that showed that the product comprised 3-methacryloxypropyl-dimethylchlorosilane. GLC purity of the product was 97.1%. Absorbance of the obtained 3-methacryloxypropyl dimethylchlorosilane measured at 350 nm was 0.030.

Comparation Example 1

Distillation was carried out under the same conditions as in Application Example 1, but without the use of the tung oil. The residue comprised 82 g of a low-viscosity brown liquid. 214 g of the obtained distillation fraction was analyzed by gas chromatography analysis that showed that the product comprised 3-methacryloxypropyl dimethylchlorosilane. GLC purity of the product was 97.5%. However, the fraction had a yellow color. Absorbance of the obtained 3-methacryloxypropyl dimethylchlorosilane measured at 350 nm was 0.060.

The invention claimed is:

1. A method for distillation of organosilicon compounds that contain acryloxy or methacryloxy groups characterized by subjecting an organosilicon compound (A) that contains acryloxy or methacryloxy groups to distillation in the presence of:

a polymerization inhibitor (B) of the following general formula (1):

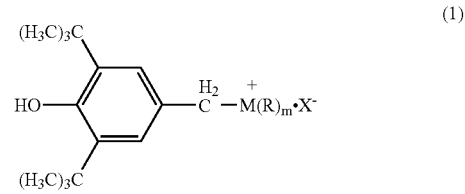

or of the following general formula (2):

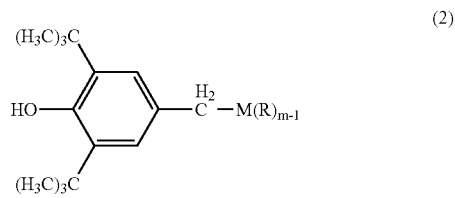

(where M is an atom selected from the group consisting of N, P, As, Sb, O, S, Se, Sn and I; R is a monovalent hydrocarbon group or a hydrogen atom; m is 1, 2 or 3; and X is a conjugated base of an organic acid or inorganic acid); and a compound (C) with aliphatic conjugated unsaturated bonds.

2. The method of distillation according to claim 1, wherein said component (B) is a polymerization inhibitor in which M of formula (1) is a nitrogen atom.

3. The method of distillation according to claim 1, wherein said component (B) is represented by the following formula (3):

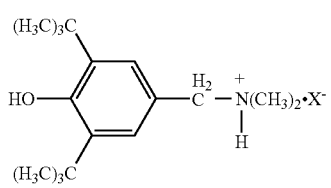

(3)

or by the following formula (4):

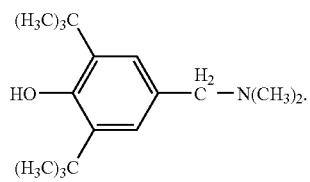

(4)

4. The method of distillation according to claim 1, wherein said component (C) is selected from the group consisting of a conjugated linolic acid, dehydrated castor oil, tung oil, α-eleostearic acid, and cyclooctatetraene.

5. The method of distillation according to claim 1, wherein said component (A) is 3-methacryloxypropyl-dimethylchlorosilane.

6. The method of distillation according to claim 1, wherein distillation is caffied out in the presence of copper chloride.

7. The method of distillation according to claim 6, wherein distillation is carried out in the presence of an antioxidant selected from the group consisting of a hindered phenol compound (with the exception of said component (B)), an amine-type compound, and a quinone-type compound.

8. The method of distillation according to claim 2, wherein said component (C) is selected from the group consisting of a conjugated linolic acid, dehydrated castor oil, tung oil, α-eleostearic acid, and cyclooctatetraene.

9. The method of distillation according to claim 3, wherein said component (C) is selected from the group consisting of a conjugated linolic acid, dehydrated castor oil, tung oil, α-eleostearic acid, and cyclooctatetraene.

10. The method of distillation according to claim 5, wherein distillation is carried out in the presence of copper chloride.

11. The method of distillation according to claim 10, wherein distillation is carried out in the presence of an antioxidant selected from the group consisting of a hindered phenol compound (with the exception of said component (B)), an amine-type compound, and a quinone-type compound.

* * * * *

UNITED STATES PATENT AND TRADEMARK OFFICE
CERTIFICATE OF CORRECTION

PATENT NO. : 7,335,784 B2  Page 1 of 1
APPLICATION NO. : 10/550822
DATED : February 26, 2008
INVENTOR(S) : Satoshi Onodera et al.

It is certified that error appears in the above-identified patent and that said Letters Patent is hereby corrected as shown below:

Column 17, line 7, after "distillation is," delete "caffied" insert therein -- carried --.

Signed and Sealed this

Second Day of September, 2008

JON W. DUDAS
*Director of the United States Patent and Trademark Office*